*(12)* United States Patent
Kaifosh et al.

(10) Patent No.: US 10,409,371 B2
(45) Date of Patent: Sep. 10, 2019

(54) METHODS AND APPARATUS FOR INFERRING USER INTENT BASED ON NEUROMUSCULAR SIGNALS

(71) Applicant: CTRL-labs Corporation, New York, NY (US)

(72) Inventors: Patrick Kaifosh, New York, NY (US); Timothy Machado, Palo Alto, CA (US); Thomas Reardon, New York, NY (US); Erik Schomburg, Brooklyn, NY (US)

(73) Assignee: CTRL-labs Corporation, New York, NY (US)

( * ) Notice: Subject to any disclaimer, the term of this patent is extended or adjusted under 35 U.S.C. 154(b) by 154 days.

(21) Appl. No.: 15/659,018

(22) Filed: Jul. 25, 2017

(65) Prior Publication Data

US 2018/0024634 A1 Jan. 25, 2018

Related U.S. Application Data

(60) Provisional application No. 62/366,419, filed on Jul. 25, 2016.

(51) Int. Cl.
*G06F 3/01* (2006.01)
*A61B 5/0488* (2006.01)
(Continued)

(52) U.S. Cl.
CPC ............ *G06F 3/015* (2013.01); *A61B 5/0488* (2013.01); *A61B 5/7267* (2013.01); *G06N 7/005* (2013.01); *G06N 20/00* (2019.01); *A61B 5/7282* (2013.01)

(58) Field of Classification Search
None
See application file for complete search history.

(56) References Cited

U.S. PATENT DOCUMENTS 6,005,548 A 12/1999 Latypov et al.
6,009,210 A 12/1999 Kand
(Continued)

FOREIGN PATENT DOCUMENTS

CA 2902045 A1 8/2014
CA 2921954 A1 2/2015
(Continued)

OTHER PUBLICATIONS

International Search Report and Written Opinion for International Application No. PCT/US2017/043686 dated Oct. 6, 2017.
(Continued)

*Primary Examiner* — Chad M Dicke
(74) *Attorney, Agent, or Firm* — Wolf, Greenfield & Sacks, P.C.

(57) ABSTRACT

Methods and system for predicting the onset of a motor action using neuromuscular signals. The system comprises a plurality of sensors configured to continuously record a plurality of neuromuscular signals from a user and at least one computer processor programmed to provide as input to a trained statistical model, the plurality of neuromuscular signals or information based on the plurality of neuromuscular signals, predict, based on an output of the trained statistical model, whether an onset of a motor action will occur within a threshold amount of time; and send a control signal to at least one device based, at least in part, on the output probability, wherein the control signal is sent to the at least one device prior to completion of the motor action by the user.

20 Claims, 6 Drawing Sheets

(51) Int. Cl.
  *G06N 7/00* (2006.01)
  *G06N 20/00* (2019.01)
  *A61B 5/00* (2006.01)

(56) References Cited

U.S. PATENT DOCUMENTS

| | | | |
|---|---|---|---|
| 6,244,873 B1 | 6/2001 | Hill et al. | |
| 6,658,287 B1 * | 12/2003 | Litt | A61B 5/0476 600/544 |
| 6,720,984 B1 | 4/2004 | Jorgensen et al. | |
| 7,089,148 B1 | 8/2006 | Bachmann et al. | |
| 7,351,975 B2 | 4/2008 | Brady et al. | |
| 7,574,253 B2 | 8/2009 | Edney et al. | |
| 7,580,742 B2 | 8/2009 | Tan et al. | |
| 7,805,386 B2 | 9/2010 | Greer | |
| 8,170,656 B2 | 5/2012 | Tan et al. | |
| 8,190,249 B1 | 5/2012 | Gharieb et al. | |
| 8,311,623 B2 * | 11/2012 | Sanger | A61B 5/0488 600/546 |
| 8,351,651 B2 | 1/2013 | Lee | |
| 8,421,634 B2 | 4/2013 | Tan et al. | |
| 8,435,191 B2 | 5/2013 | Barboutis et al. | |
| 8,437,844 B2 | 5/2013 | Momen et al. | |
| 8,447,704 B2 * | 5/2013 | Tan | G06F 3/015 706/12 |
| 8,484,022 B1 | 7/2013 | Vanhoucke | |
| 8,754,862 B2 | 6/2014 | Zaliva | |
| 8,880,163 B2 | 11/2014 | Barachant et al. | |
| 8,890,875 B2 | 11/2014 | Jammes et al. | |
| 8,892,479 B2 | 11/2014 | Tan et al. | |
| 9,037,530 B2 | 5/2015 | Tan et al. | |
| 9,218,574 B2 | 12/2015 | Phillipps et al. | |
| 9,235,934 B2 | 1/2016 | Mandella et al. | |
| 9,240,069 B1 | 1/2016 | Li | |
| 9,278,453 B2 | 3/2016 | Assad | |
| 9,299,248 B2 | 3/2016 | Lake et al. | |
| 9,367,139 B2 | 6/2016 | Ataee et al. | |
| 9,372,535 B2 | 6/2016 | Bailey et al. | |
| 9,389,694 B2 | 7/2016 | Ataee et al. | |
| 9,408,316 B2 | 8/2016 | Bailey et al. | |
| 9,459,697 B2 | 10/2016 | Bedikian et al. | |
| 9,483,123 B2 | 11/2016 | Aleem et al. | |
| 9,600,030 B2 | 3/2017 | Bailey et al. | |
| 9,612,661 B2 | 4/2017 | Wagner et al. | |
| 9,613,262 B2 | 4/2017 | Holz | |
| 9,659,403 B1 | 5/2017 | Horowitz | |
| 9,687,168 B2 | 6/2017 | John | |
| 9,696,795 B2 | 7/2017 | Marcolina et al. | |
| 9,720,515 B2 | 8/2017 | Wagner et al. | |
| 9,741,169 B1 | 8/2017 | Holz | |
| 9,766,709 B2 | 9/2017 | Holz | |
| 9,785,247 B1 | 10/2017 | Horowitz et al. | |
| 9,788,789 B2 | 10/2017 | Bailey | |
| 9,864,431 B2 | 1/2018 | Keskin et al. | |
| 9,867,548 B2 | 1/2018 | Le et al. | |
| 9,880,632 B2 | 1/2018 | Ataee et al. | |
| 9,891,718 B2 * | 2/2018 | Connor | G06F 3/017 |
| 10,042,422 B2 | 8/2018 | Morun et al. | |
| 10,070,799 B2 | 9/2018 | Ang et al. | |
| 10,101,809 B2 | 10/2018 | Morun et al. | |
| 10,152,082 B2 | 12/2018 | Bailey | |
| 10,188,309 B2 | 1/2019 | Morun et al. | |
| 10,199,008 B2 | 2/2019 | Aleem et al. | |
| 10,203,751 B2 | 2/2019 | Keskin et al. | |
| 10,216,274 B2 | 2/2019 | Chapeskie et al. | |
| 2003/0144829 A1 | 7/2003 | Geatz et al. | |
| 2007/0256494 A1 | 11/2007 | Nakamura et al. | |
| 2008/0221487 A1 | 9/2008 | Zohar et al. | |
| 2010/0106044 A1 | 4/2010 | Linderman | |
| 2010/0280628 A1 | 11/2010 | Sankai | |
| 2010/0292617 A1 | 11/2010 | Lei et al. | |
| 2010/0293115 A1 | 11/2010 | Seyed Momen | |
| 2010/0315266 A1 * | 12/2010 | Gunawardana | G06F 3/0237 341/22 |
| 2012/0066163 A1 * | 3/2012 | Balls | C12Q 1/6886 706/21 |
| 2012/0283526 A1 | 11/2012 | Gommesen et al. | |
| 2013/0077820 A1 | 3/2013 | Marais et al. | |
| 2014/0092009 A1 | 4/2014 | Yen et al. | |
| 2014/0098018 A1 | 4/2014 | Kim et al. | |
| 2014/0196131 A1 | 7/2014 | Lee | |
| 2014/0198034 A1 | 7/2014 | Bailey et al. | |
| 2014/0198035 A1 | 7/2014 | Bailey et al. | |
| 2014/0240103 A1 | 8/2014 | Lake et al. | |
| 2014/0240223 A1 | 8/2014 | Lake et al. | |
| 2014/0245200 A1 | 8/2014 | Holz | |
| 2014/0249397 A1 | 9/2014 | Lake et al. | |
| 2014/0334083 A1 | 11/2014 | Bailey | |
| 2014/0344731 A1 | 11/2014 | Holz | |
| 2014/0376773 A1 | 12/2014 | Holz | |
| 2015/0025355 A1 | 1/2015 | Bailey et al. | |
| 2015/0029092 A1 | 1/2015 | Holz et al. | |
| 2015/0051470 A1 | 2/2015 | Bailey et al. | |
| 2015/0057770 A1 | 2/2015 | Bailey et al. | |
| 2015/0070270 A1 | 3/2015 | Bailey et al. | |
| 2015/0084860 A1 | 3/2015 | Aleem et al. | |
| 2015/0109202 A1 | 4/2015 | Ataee et al. | |
| 2015/0124566 A1 | 5/2015 | Lake et al. | |
| 2015/0141784 A1 | 5/2015 | Morun et al. | |
| 2015/0148641 A1 | 5/2015 | Morun et al. | |
| 2015/0157944 A1 | 6/2015 | Gottlieb | |
| 2015/0169074 A1 | 6/2015 | Ataee et al. | |
| 2015/0193949 A1 | 7/2015 | Katz et al. | |
| 2015/0234426 A1 | 8/2015 | Bailey et al. | |
| 2015/0261306 A1 * | 9/2015 | Lake | G06F 3/017 340/5.1 |
| 2015/0277575 A1 | 10/2015 | Ataee et al. | |
| 2015/0309582 A1 | 10/2015 | Gupta | |
| 2015/0325202 A1 | 11/2015 | Lake et al. | |
| 2015/0346701 A1 | 12/2015 | Gordon et al. | |
| 2015/0370326 A1 | 12/2015 | Chapeskie et al. | |
| 2015/0370333 A1 | 12/2015 | Ataee et al. | |
| 2016/0262687 A1 | 9/2016 | Imperial | |
| 2016/0274758 A1 | 9/2016 | Bailey | |
| 2016/0313801 A1 | 10/2016 | Wagner et al. | |
| 2016/0313899 A1 | 10/2016 | Noel | |
| 2017/0124816 A1 | 5/2017 | Yang et al. | |
| 2018/0064363 A1 | 3/2018 | Morun et al. | |
| 2018/0067553 A1 | 3/2018 | Morun et al. | |
| 2018/0088765 A1 | 3/2018 | Bailey | |
| 2018/0095630 A1 | 4/2018 | Bailey | |
| 2018/0101289 A1 | 4/2018 | Bailey | |
| 2018/0120948 A1 | 5/2018 | Aleem et al. | |
| 2018/0150033 A1 | 5/2018 | Lake et al. | |
| 2018/0153444 A1 | 6/2018 | Yang et al. | |
| 2018/0307314 A1 | 10/2018 | Connor | |
| 2018/0344195 A1 | 12/2018 | Morun et al. | |
| 2018/0360379 A1 | 12/2018 | Harrison et al. | |

FOREIGN PATENT DOCUMENTS

| | | |
|---|---|---|
| CA | 2939644 A1 | 8/2015 |
| CN | 1838933 A | 9/2006 |
| CN | 105190578 A | 12/2015 |
| CN | 106102504 A | 11/2016 |
| EP | 2959394 A1 | 12/2015 |
| EP | 3104737 A1 | 12/2016 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| WO | WO 2014/130871 A1 | 8/2014 |
| WO | WO 2014/186370 A1 | 11/2014 |
| WO | WO 2014/194257 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |

(56) References Cited

FOREIGN PATENT DOCUMENTS

WO     WO 2016/041088 A1     3/2016
WO     WO 2017/092225 A1     6/2017

OTHER PUBLICATIONS

International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Gallina et al., Surface EMG Biofeedback. Surface Electromyography: Physiology, Engineering, and Applications. 2016:485-500.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Li et al., Motor Function Evaluation of Hemiplegic Upper-Extremities Using Data Fusion from Wearable Inertial and Surface EMG Sensors. Sensors. MDPI. 2017;17(582):1-17.
McIntee, A Task Model of Free-Space Movement-Based Geastures. Dissertation. Graduate Faculty of North Carolina State University. Computer Science. 2016. 129 pages.
Naik et al., Source Separation and Identification issues in bio signals: A solution using Blind source seperation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.

* cited by examiner

METHODS AND APPARATUS FOR INFERRING USER INTENT BASED ON NEUROMUSCULAR SIGNALS

CROSS-REFERENCE TO RELATED APPLICATIONS

This application claims the benefit under 35 U.S.C. § 119(e) of U.S. Provisional Patent Application Ser. No. 62/366,419, filed Jul. 25, 2016, and entitled "Method and apparatus for inferring user intention," the entire contents of which is incorporated by reference herein.

BACKGROUND

Neuromuscular signals arising from the human central nervous system provide information about neural activation that results in the contraction of one or more muscles in the human body. The neuromuscular signals may measure the neural activation, the muscle excitation, the muscle contraction, or a combination of the neural activation and the muscle contraction. Electromyography (EMG) sensors placed on the surface of the human body record electrical activity produced by skeletal muscle cells upon their activation. Signals recorded by EMG sensors are routinely used to assess neuromuscular dysfunction in patients with motor control disorders and have been used in some applications as control signals for devices such as prosthetic limbs.

SUMMARY

Biophysical sensors such as EMG sensors record biological signals in advance of the onset of motor activity. In the case of EMG sensors arranged on the surface of the human body, the biological signals recorded relate to the generation of action potentials in muscle fibers of muscles of the human body. Some embodiments are directed to analyzing EMG signals using a trained statistical model to predict the onset of a motor task prior to performance of the motor task. Control signals determined based on the model predictions may be used to control the operation of devices with short latency.

Controlling devices based, at least in part, on a reliable prediction of an onset of motor task rather than waiting until a user has completed the motor task provides for an improvement to conventional techniques for controlling devices. Non-limiting illustrative applications include replacements or enhancements for buttons or triggers/switches for games that require fast reaction times, steering or other operating inputs for physical or virtual vehicles including cars, enhanced control of joysticks or navigational controls, and manipulation of objects within a virtual reality environment, such as picking up or throwing virtual balls.

Some embodiments are directed to a control system. The control system comprises a plurality of sensors configured to continuously record a plurality of neuromuscular signals from a user, and at least one computer processor programmed to provide as input to a trained statistical model, the plurality of neuromuscular signals and/or information based on the plurality of neuromuscular signals, predict, based on an output of the trained statistical model, whether an onset of a motor action will occur within a threshold amount of time, and send a control signal to at least one device based, at least in part, on the output probability, wherein the control signal is sent to the at least one device prior to completion of the motor action by the user.

Other embodiments are directed to at least one non-transitory computer readable medium encoded with a plurality of instructions that, when executed by at least one computer processor perform a method. The method comprises providing, as input to a trained statistical model, a plurality of neuromuscular signals recorded from a plurality of sensors arranged on or around a part of a user's body, predicting whether an onset of a motor action will occur within a threshold amount of time, and sending a control signal to at least one device based, at least in part, on the output probability, wherein the control signal is sent to the at least one device prior to completion of the motor action by the user.

Other embodiments are directed to a method of predicting an onset of a motor action. The method comprises providing, as input to a trained statistical model, a plurality of neuromuscular signals recorded from a plurality of sensors arranged on or around a part of a user's body, predicting, using at least one computer processor, whether an onset of a motor action will occur within a threshold amount of time, and sending a control signal to at least one device based, at least in part, on the output probability, wherein the control signal is sent to the at least one device prior to completion of the motor action by the user.

Other embodiments are directed to a computer system for training a statistical model to predict an onset of a motor task based, at least in part, on neuromuscular signal data. The computer system comprises an input interface configured to receive the neuromuscular signal data recorded during performance of a motor action performed by one or more users, receive result data indicating an outcome of the motor action performed by the one or more users. The computer system further comprises at least one storage device configured to store a plurality of instructions that, when executed by at least one computer processor perform a method of generating training data based, at least on part, on the received neuromuscular signal data and the received result data, training the statistical model using at least some of the generated training data to output a trained statistical model, determining an operating threshold used to interpret output of the trained statistical model, and storing, by the at least one storage device, the trained statistical model and the operating threshold, wherein the trained statistical model is configured to predict the onset of a motor task prior to completion of the motor task by a user.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

DETAILED DESCRIPTION

Coordinated movements of skeletal muscles in the human body that collectively result in the performance of a motor task originate with neural signals arising in the central nervous system. The neural signals travel from the central nervous system to muscles via spinal motor neurons, each of which has a body in the spinal cord and axon terminals on one or more muscle fibers. In response to receiving the neural signals, the muscle fibers contract resulting in muscle movement.

Figure 1:
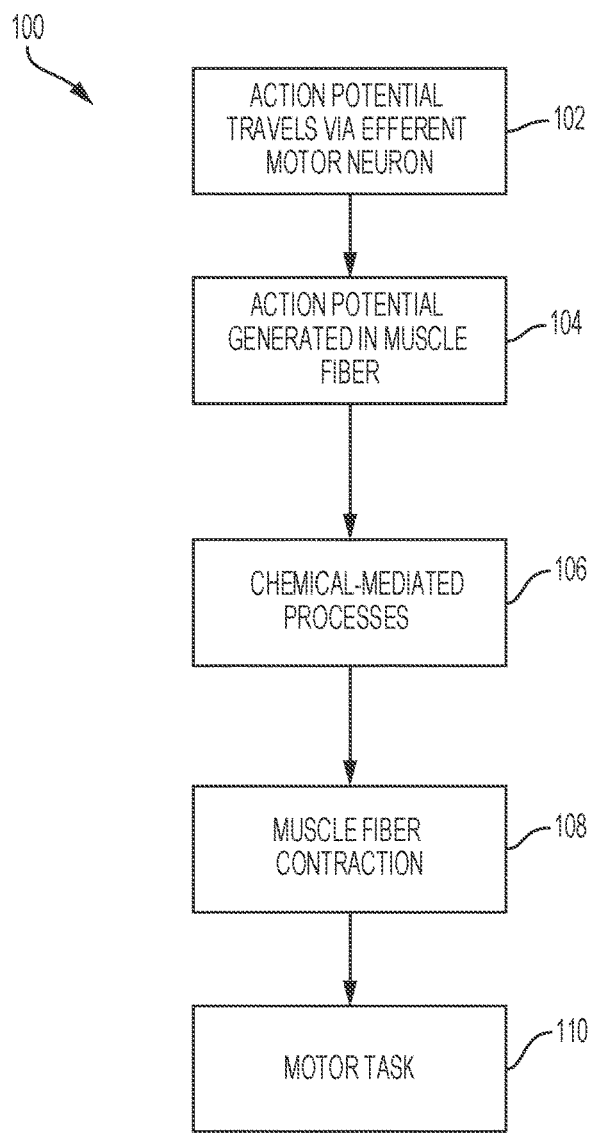
FIG. 1 is a flowchart of a biological process for performing a motor task in accordance with some embodiments of the technology described herein.

FIG. 1 illustrates a flowchart of a biological process 100 for initiating a motor task by the coordinated movement of one or more muscles. In act 102, action potentials are generated in one or more efferent spinal motor neurons. The motor neurons carry the neuronal signal away from the central nervous system and toward skeletal muscles in the periphery. For each motor neuron in which an action potential is generated, the action potential travels along the axon of motor neuron from its body in the spinal cord where the action potential is generated to the axon terminals of the motor neuron that innervate muscle fibers included in skeletal muscles.

A chemical synapse formed at the interface between an axon terminal of a spinal motor neuron and a muscle fiber is called a neuromuscular junction. As an action potential transmitted along the axon of a motor neuron reaches the neuromuscular junction, process 100 proceeds to act 104, where an action potential is generated in the muscle fiber as a result of chemical activity at the neuromuscular junction. In particular, Acetylcholine released by the motor neuron diffuses across the neuromuscular junction and binds with receptors on the surface of the muscle fiber triggering a depolarization of the muscle fiber. Although neuromuscular signals sensed on the body surface generated by individual muscle fibers are small (e.g., less than 100 µV), the collective action of multiple muscle fibers conducting simultaneously results in a detectable voltage potential that may be recorded by neuromuscular (e.g., EMG) sensors located on the surface of the body.

Following generation of an action potential in the muscle fiber, process 100 proceeds to act 106, where the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes causing the troponin complexes to separate from myosin binding sites on actin filaments in the muscle fiber, thereby exposing the myosin binding sites.

Following these chemical-mediated processes, process 100 proceeds to act 108, where the muscle fiber contracts. Muscle fiber contraction is achieved due to the binding of exposed myosin heads with actin filaments in the muscle fiber creating cross-bridge structures. Process 100 then proceeds to act 110, where the collective contraction of muscle fibers in one or more muscles results in the performance of a motor task. The motor task may be a simple task such as a button press, which involves only a few muscles in a finger and/or wrist, a more complex task such as grasping and turning a doorknob involving several muscles of the hand, wrist and arm, or a motor task of any other complexity, as embodiments of the technology described herein are not limited in this respect.

Neural activity, muscle fiber recruitment, muscle contraction and joint movement all precede the completion of a motor task. For example, the chemical-mediated and mechanical processes involved in acts 106 and 108 of process 100 are not instantaneous, but occur over a time period, which may be on the order of hundreds of milliseconds. Accordingly, there is a time delay between when neuromuscular sensors placed on or near the body surface record the generation of action potentials in the muscle fibers at act 104 in process 100 and when the motor task is performed in act 110. The inventors have recognized and appreciated that rather than waiting until the intentional action is performed, signals recorded from neuromuscular sensors may be used to predict the motor task to be performed in advance of the task actually being performed by the wearer of the sensors.

Throughout this disclosure electromyography (EMG) sensors are used as examples of the type of neuromuscular sensors configured to detect neuromuscular activity. However it should be appreciated that other types of neuromuscular sensors including, but not limited to, mechanomyography (MMG) sensors and sonomyography (SMG) sensors may additionally or alternatively be used in combination with EMG sensors to detect neuromuscular activity in accordance with some embodiments. The neuromuscular signals recorded by the neuromuscular sensors may be used to predict the onset of one or more motor tasks being performed by the wearer of such sensors.

Accordingly, some embodiments are directed to predicting with short latency (e.g., prior to a motor task being performed), based on recorded neuromuscular signals (e.g., EMG signals, MMG signals, and SMG signals), the onset of the motor task using a statistical model trained to model neuromuscular activity leading to the performance of the motor task. In some embodiments, the neuromuscular signals are recorded continuously and predictions are made based on the continuously recorded neuromuscular signals. As a non-limiting example of a simple motor task of pressing a button, some embodiments determine, based on a plurality of neuromuscular signals, a likelihood that the button will be pressed prior to the user actually pressing the button. In some embodiments the prediction can be made 10 milliseconds prior to the action being performed, in other embodiments the prediction can be made 50 milliseconds, 100 milliseconds, 200 milliseconds, or 250 milliseconds prior to the task being performed. The prediction may be made 50-100 milliseconds, 100-200 milliseconds, or 200-300 milliseconds prior to the task being performed in some embodiments. The prediction of a user's intention to perform a motor task in accordance with some embodiments can be used to control devices at short latency, as discussed in more detail below.

Figure 2:
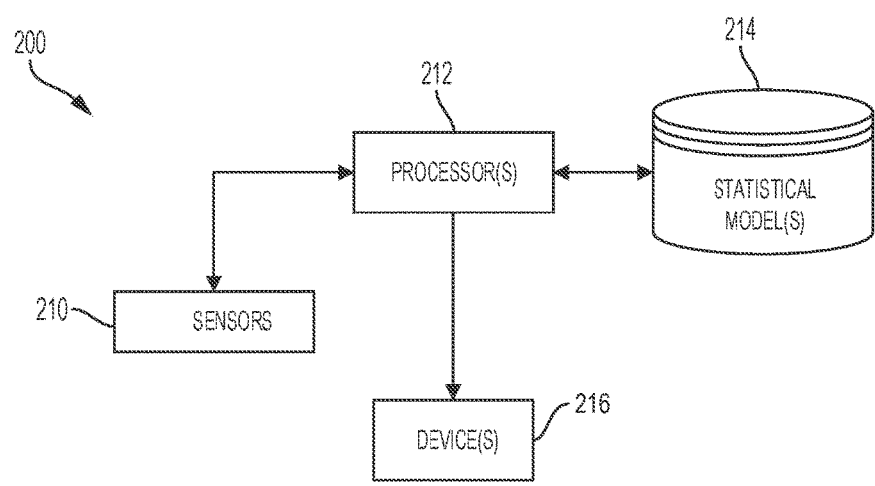
FIG. 2 is a schematic diagram of a computer-based system for predicting an onset of one or more motor tasks in accordance with some embodiments of the technology described herein.

FIG. 2 illustrates a system 200 in accordance with some embodiments. The system includes a plurality of neuromuscular sensors 210 configured to record signals arising from neuromuscular activity in skeletal muscle of a human body. Neuromuscular sensors 210 may include one or more EMG sensors, one or more MMG sensors, one or more SMG sensors, and/or one or more sensors of any suitable type that are configured to detect neuromuscular signals. Typical EMG sensors include electrodes which detect electric potentials on the surface of the body and hardware processing circuitry that processes the raw EMG signal to perform amplification, filtering (e.g., low pass, high pass, band pass, shaping, narrow band, wide band, temporal etc.), or other types of signal processing (e.g., rectification). Some embodiments employ EMG sensors including hardware signal processing circuitry for processing recorded EMG signals. Other embodiments employ EMG sensors, where at least some of the processing circuitry is performed by one or more circuits in communication with, but not directly integrated with the electrodes that record the signals. In other embodiments, at least some (e.g., all) of the signal processing (e.g., amplification, filtering, rectification, etc.) may be implemented using software rather than by using hardware signal processing circuitry. Thus, signal processing of EMG signals (e.g., amplification, filtering, and rectification) may be performed in hardware only, in software only, or by any combination of hardware and software, as aspects of the technology described herein are not limited in this respect.

In some embodiments, neuromuscular sensors 210 include one or more MMG sensors and/or one or more SMG sensors in addition to or instead of EMG sensors. When used, MMG and SMG sensors may be of any suitable type, as aspects of the technology described herein are not limited in this respect. Some embodiments employ MMG and/or SMG sensors that include hardware signal processing circuitry for performing signal processing (e.g., amplification, filtering, and rectification) on recorded MMG and/or SMG signals. In other embodiments, at least some signal processing of the MMG and/or SMG signals may be performed in software. Thus, signal processing of MMG and/or SMG signals may be performed in hardware only, in software only, or by any suitable combination of hardware and software, as aspects of the technology described herein are not limited in this respect.

In some embodiments, the plurality of neuromuscular sensors 210 includes one or more pairs of neuromuscular sensors arranged as a portion of a wearable device configured to be worn on or around part of a user's body. For example, in one non-limiting example, a plurality of neuromuscular sensors may be arranged circumferentially around an adjustable and/or elastic band such as a wristband or armband configured to be worn around a user's wrist or arm.

Figure 5A:
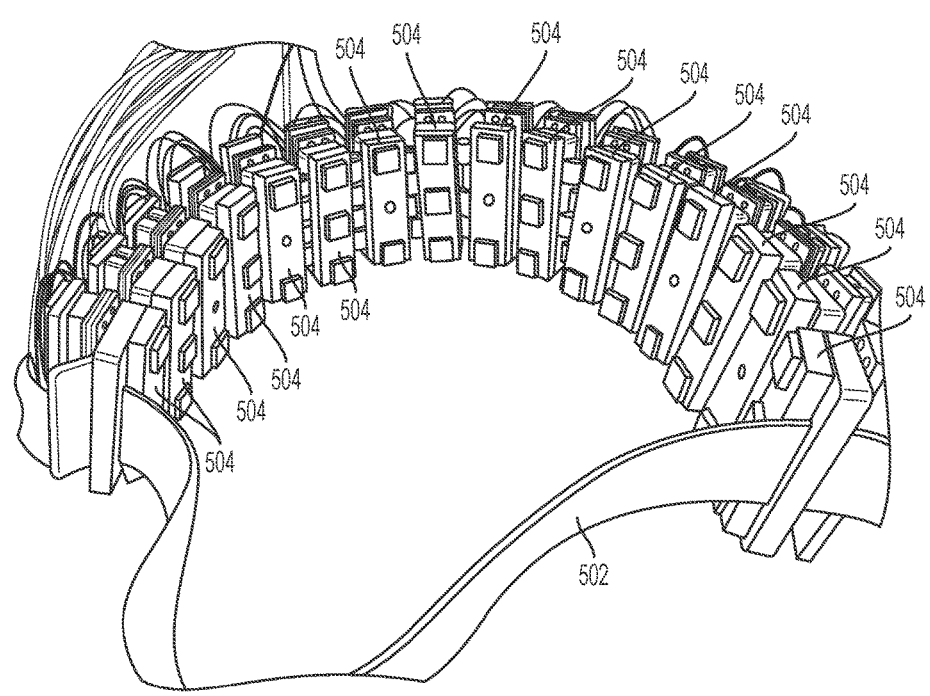
FIG. 5A illustrates a wristband having EMG sensors arranged circumferentially thereon, in accordance with some embodiments of the technology described herein.
Figure 5B:
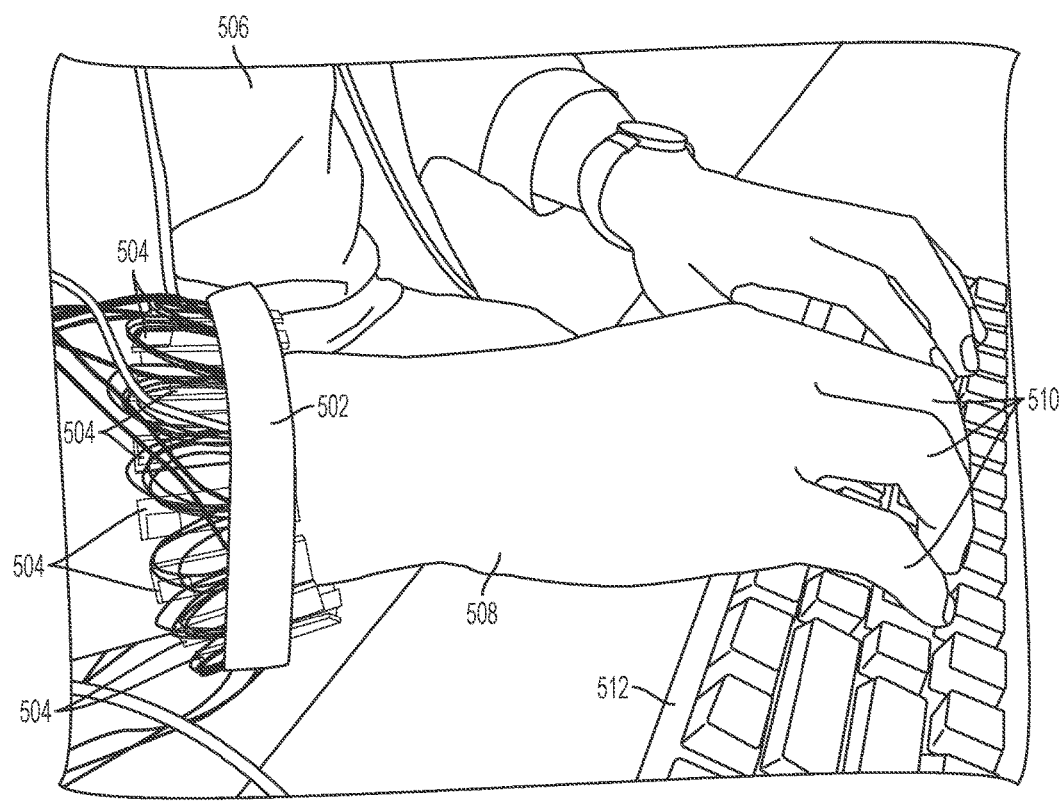
FIG. 5B illustrates a user wearing the wristband of FIG. 5A while typing on a keyboard, in accordance with some embodiments of the technology described herein.

In one implementation, 16 EMG sensors are arranged circumferentially around an elastic band configured to be worn around a user's lower arm. For example, FIG. 5A shows EMG sensors 504 arranged circumferentially around elastic band 502. It should be appreciated that any suitable number of EMG sensors may be used and the particular number and arrangement of EMG sensors used may depend on the particular application for which the wearable device is used. For example, a wearable armband or wristband may be used to predict hand-based motor tasks such as pressing button or moving a joystick, whereas a wearable leg or ankle band may be used to predict foot-based motor tasks such as pressing the gas or brake pedal on a vehicle such as a real or virtual car. For example, as shown in FIG. 5B, a user 506 may be wearing elastic band 502 on hand 508. In this way, EMG sensors 504 may be configured to record EMG signals as a user controls keyboard 512 using fingers 510.

In some embodiments, multiple wearable devices, each having one or more EMG sensors included thereon may be used to predict the onset of complex motor tasks that involve multiple parts of the body.

System 200 also includes one or more computer processors 212 programmed to communicate with sensors 210. For example, signals recorded by sensors 210 may be provided to processor(s) 212 for processing. Processor(s) 212 may be implemented in hardware, firmware, software, or any combination thereof. Additionally, processor(s) 212 may be co-located on the same wearable device as the neuromuscular sensors 210 or may be at least partially located remotely (e.g., processing may occur on one or more network-connected processors).

System 200 also includes datastore 214 in communication with processor(s) 212. Datastore 214 may include one or more storage devices configured to store information describing a statistical model used for prediction of the onset of motor tasks in accordance with some embodiments. Processor(s) 212 may be configured to execute one or more machine learning algorithms that process signals output by the sensor(s) 210 to train a statistical model stored in datastore 214, and the trained (or retrained) statistical model may be stored in datastore 214 for later use in predicting the onset of a motor task. Non-limiting examples of statistical models that may be used in accordance with some embodiments to predict the onset of a motor task based on recorded neuromuscular signals are discussed in more detail below.

In some embodiments, processor(s) 212 may be configured to communicate with neuromuscular sensors 210, for example to calibrate the sensors prior to measurement of neuromuscular signals. For example, a wearable device may be positioned in different orientations on or around a part of a user's body and calibration may be performed to determine the orientation of the wearable device and/or to perform any other suitable calibration tasks. Calibration of neuromuscular sensors 210 may be performed in any suitable way, and embodiments are not limited in this respect. For example, in some embodiments, a user may be instructed to perform a particular sequence of movements and the recorded neuromuscular activity may be matched to a template by virtually rotating and/or scaling the signals detected by the sensors (e.g., by the electrodes on EMG sensors). In some embodiments, calibration may involve changing the gain(s) of one or more analog to digital converters (ADCs), for example, in the case that the signals detected by the sensors result in saturation of the ADCs.

System 200 also includes one or more devices 216 configured to be controlled based, at least in part, on processing by processor(s) 212. As discussed in more detail below, processor(s) 212 may implement a trained statistical model 214 configured to predict the onset of a motor task based, at least in part, on neuromuscular signals recorded by sensors 210 (e.g., EMG sensors, MMG sensors, and SMG sensors), and one or more control signals determined based on the predicted onset of the motor task may be sent to device 216 to control one or more operations of the device with a latency shorter than would be achieved if the control signal was not sent until motor task completion. In some embodiments, device 216 may be controlled with a latency of a duration that is not perceptible, difficult to perceive, or unlikely to be perceived by humans, or with a latency of a duration that is imperceptible to a person with ordinary sensory perception.

Device 216 may include any device configured to receive control signals through a control interface. Non-limiting examples of devices include consumer electronics devices (e.g., television, smartphone, computer, laptop, telephone, video camera, photo camera, video game system, appliance, etc.), vehicles (e.g., car, marine vessel, manned aircraft, unmanned aircraft, farm machinery, etc.), robots, weapons, or any other device that may receive control signals through one or more control interfaces.

A device 216 may be controlled through any suitable type of control interface. A control interface may be implemented using hardware, software, or any suitable combination thereof. For example, a device 216 may be a video game system which may be controlled through a game controller. As another example, a device 216 may be a computing device, which may be controlled through a keyboard, keypad, and/or a mouse. As another example, a device may be a computing device, which may be touch controlled through a graphical user interface generated by a touch-screen display. As another example, a device may be a vehicle (e.g., a car, an aircraft, a marine vessel, an unmanned aerial vehicle, etc.), which may be controlled through one or more mechanical control devices (e.g., pedals, wheel, joystick, paddles, levers, knobs, etc.).

In some embodiments, system 200 may be trained to predict the onset of one or more motor actions performed by the user. The motor actions may include control actions a user takes with respect to a control interface of a device of devices 216. For example, when the control interface of a device includes one or more buttons, the system 200 may be trained to predict whether a user will press one or more of the buttons within a threshold amount of time. In some embodiments, the system 200 may be trained by recording the neuromuscular signals of one or more users as the user(s) provide input through a control interface of a device. After such training, the system 200 may be configured to predict, based on a particular user's neuromuscular signals, whether the user will perform one or more control actions with respect to the control interface.

In some embodiments, after system 200 is trained to predict, based on a particular user's neuromuscular signals, whether the user will perform one or more control actions with respect to the control interface of a device, a user may utilize the system 200 to control the device without the control interface. For example, when the system 200 is trained to predict the control actions that the user intends to take with high accuracy (e.g., at least a threshold accuracy), the predictions themselves may be used to control the device.

In some embodiments, a user may utilize a combination of the system 200 and the control interface to control a device. For example, when the system 200 generates a prediction of the control action that the user will take with respect to the control interface and the prediction is generated with at least a threshold amount of confidence and/or within a threshold amount of time of when the predicted action is to take place, the prediction may be used to generate a control signal and the system 200 may control the device. On the other hand, if the prediction is generated with lower than a threshold confidence or is generated too far in advance, the system 200 may be configured to not use such a prediction to control the device. In that case, the user may control the device directly through the control interface.

Some embodiments include a feedback system configured to be initiated based on a control signal provided processor(s) 212 in accordance with some embodiments. The feedback system may represent a final motor task to be performed and may be initiated simultaneously with task completion. In some embodiments, the feedback system may be configured to provide feedback using haptic technology or using a buzzer system.

Figure 3:
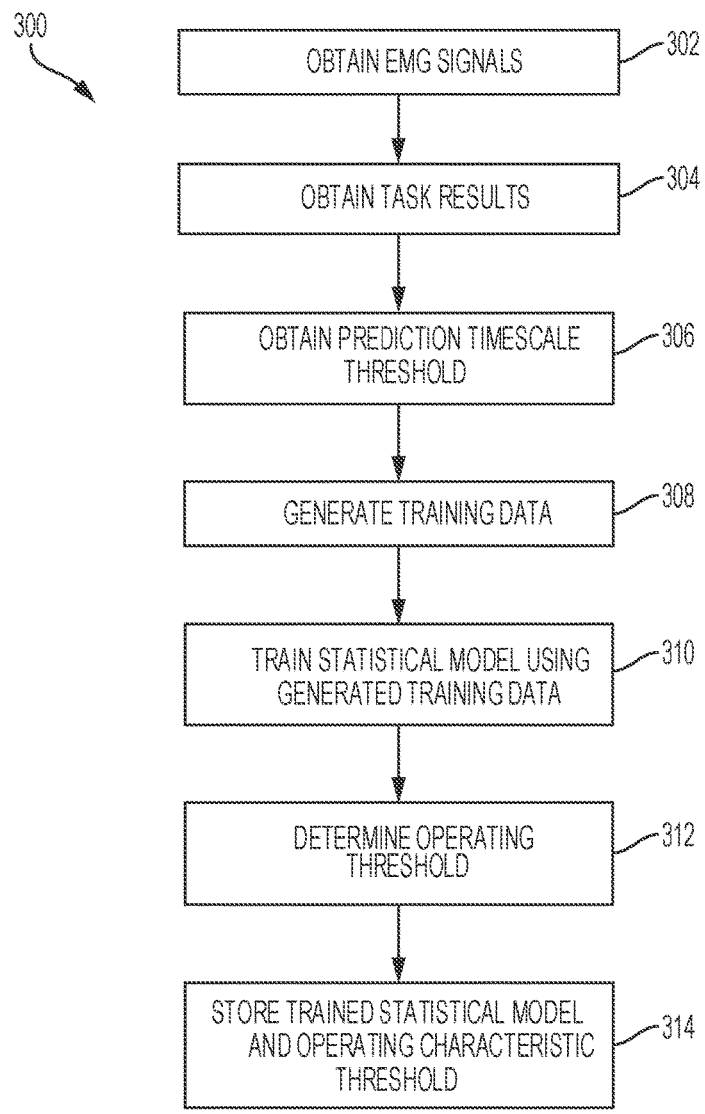
FIG. 3 is a flowchart of an illustrative process for generating a statistical model for predicting the onset of one or more motor tasks using neuromuscular signals, in accordance with some embodiments of the technology described herein.

As discussed above, some embodiments are directed to using a statistical model for predicting the onset of a motor task prior to completion of the motor task by a user. The statistical model may be used to predict the onset of a motor task based on neuromuscular signals (e.g., EMG, MMG, and SMG signals) detected as a result of neuromuscular activity that occurs in advance of the motor task onset. FIG. 3 describes a process 300 for generating (sometimes termed "training" herein) such a statistical model from EMG signals recorded for one or more users prior to the user(s) performing one or more motor task(s). Although process 300 is described herein with respect to EMG signals, it should be appreciated that process 300 may be used to train a statistical model for predicting the onset of a motor task based on EMG signals, MMG signals, SMG signals, or any suitable combination thereof.

Process 300 may be executed by any suitable computing device(s), as aspects of the technology described herein are not limited in this respect. For example, process 300 may be executed by processors 212 described with reference to FIG. 2. As another example, one or more acts of process 300 may be executed using one or more servers (e.g., servers part of a cloud computing environment). For example, at least a portion of act 310 relating to training of a statistical model (e.g., a neural network) may be performed using a cloud computing environment.

Process 300 begins at act 302, where a plurality of neuromuscular signals is obtained for one or multiple users performing one or more motor tasks. In some embodiments, the plurality of EMG signals may be recorded as part of process 300. In other embodiments, the plurality of EMG signals may have been recorded prior to the performance of process 300 and are accessed (rather than recorded) at act 302.

In some embodiments, the EMG signals obtained at act 302 may be pre-processed using amplification, filtering, rectification or other types of signal processing. In some embodiments, the filtering may comprise temporal filtering implemented using convolution operations and/or equivalent operations in the frequency domain (e.g., after the application of a discrete Fourier transform).

In some embodiments, the plurality of EMG signals may include EMG signals recorded for a single user performing one or multiple motor tasks. The user may be instructed to perform a motor task (e.g., pressing one of two buttons) and EMG signals corresponding to the user's neuromuscular activity may be recorded as the user performs the motor task he/she was instructed to perform. The EMG signals may be recorded by any suitable number of EMG sensors located in any suitable location(s) to detect the user's neuromuscular activity that is relevant to the motor task. For example, after a user is instructed to perform a motor task with the fingers of his/her right hand, the EMG signals may be recorded by multiple EMG sensors circumferentially (or otherwise) arranged around the user's lower right arm. As another example, after a user is instructed to perform a motor task with his/her leg (e.g., to push one of two pedals, for example, either a gas or brake pedal in a car), the EMG signals may be recorded by multiple EMG sensors circumferentially (or otherwise) arranged around the user's leg.

In some embodiments, the EMG signals may be recorded at multiple time points as a user performs a motor task. As a result, the recorded EMG signals may include EMG data obtained by multiple EMG sensors at each of multiple time points. Assuming that n EMG sensors are arranged to simultaneously measure the user's neuromuscular activity during performance of the motor task, the recorded EMG signals for the user may comprise a time series of K n-dimensional vectors $\{x_k | 1 \leq k \leq K\}$ at time points $t_1, t_2, \ldots, t_K$ prior and up to the completion of the motor task.

In some embodiments, a user may be instructed to perform a motor task multiple times and the user's neuromuscular activity may be recorded for each of multiple repetitions of the task by the user. In some embodiments, the plurality of EMG signals may include EMG signals recorded for multiple users, each of the multiple users performing the same motor task one or more times. Each of the multiple users may be instructed to perform the motor task and EMG signals corresponding to that user's neuromuscular activity may be recorded as the user performs (once or repeatedly) the motor task he/she was instructed to perform. When EMG signals are collected by multiple users which are combined to generate a statistical model, an assumption is that different users invoke similar neuromuscular activity for performing the same motor task. Collecting EMG signals from a single user performing the same task repeatedly and/or from multiple users performing the same motor task one or multiple times facilitates the collection of sufficient training data to generate a statistical model that can accurately predict the onset of a motor task prior to the performance of the motor task. In some embodiments, a user-independent statistical model may be generated based on training data corresponding to the recorded EMG signals from multiple users, and as the system is used by a user, the statistical model is retrained based on recorded EMG data such that the statistical model learns the user-dependent characteristics to refine the prediction capabilities of the system for the particular user.

In some embodiments, the plurality of EMG signals may include EMG signals recorded for a user (or each of multiple users) performing each of multiple motor tasks one or multiple times. For example, a user may be instructed to perform each of multiple tasks (e.g., pressing the first of two buttons on a keypad and pressing the second of two buttons on the keypad) and EMG signals corresponding to the user's neuromuscular activity may be recorded as the user performs each of the multiple motor tasks he/she was instructed to perform. Collecting such EMG data may facilitate developing a statistical model for predicting the onset of one of multiple different actions that may be taken by the user. For example, training data that incorporates responses to multiple actions may facilitate generating a statistical model for predicting which of multiple possible inputs a user may provide to one or more control devices (e.g., a keypad, a joystick, a mechanical control input, an input to a graphical user interface, etc.) in the user's environment.

As discussed above, the EMG data obtained at act 302 may be obtained by recording EMG signals as each of one or multiple users performs each of one or more actions one or more multiple times. The results of the tasks performed by these user(s) may be obtained at act 304 (e.g., which button was pressed, which input was provided, which controller was moved). As one non-limiting example, EMG data obtained at act 302 may include EMG signals as a user is performing the task of pressing a particular button on a keypad. In this example, information indicating which button was pressed by the user (e.g., the button "A") is obtained. In this way, the actions performed by the user(s) are recorded in addition to recording the EMG signals preceding the performance of the tasks. In some embodiments, when EMG signals are recorded prior to the execution of process 300 and are accessed at act 302, the results of the tasks performed by the users may also be recorded prior to the execution of process 300 and may be accessed at act 304. In other embodiments, the results of the tasks may be recorded at act 304.

Next, process 300 proceeds to act 306, where a prediction timescale threshold may optionally be obtained. The prediction timescale threshold provides an indication of how far into the future the statistical model being generated as part of process 300 will attempt to predict the onset of a user action. For example, if the prediction timescale threshold is set at 250 milliseconds (ms), then the trained statistical model generated as part of process 300, may be used to predict, based on EMG signals obtained from a user, the probability that the onset of a motor task will occur in the next 250 milliseconds. It should be appreciated that this prediction timescale threshold is different from the operating threshold described below with reference to act 312. The operating threshold relates to a probability threshold rather than being a time-based threshold.

Any suitable prediction timescale threshold (including no prediction timescale threshold) may be used, as aspects of the technology described herein are not limited in this respect. Setting this threshold too high (e.g., multiple seconds) may result in additional computation being performed, but is unlikely in practice to provide any added performance benefit because the neuromuscular activity being processed by the model may not correlate with the performance of the motor task performed so far in the future. For example, during that time there may have been intervening events resulting in the user changing their mind about what task to perform. Setting the prediction timescale threshold too low (e.g., on the order of microseconds) may result in reliable predictions, but such predictions may have limited value as they are close to the time when the onset of the task is performed by the user. Accordingly, in some embodiments, the prediction timescale threshold is not set at either of these extremes. In some embodiments, the prediction timescale threshold may be at least 50 ms, at least 100 ms, at least 250 ms, at least 500 ms, at least 1 s, between 50 and 250 ms, between 100 and 500 ms, between 200 ms and 800 ms, or in any other suitable range in these ranges. In embodiments in which a prediction timescale threshold is not set (or when the prediction timescale threshold is set at a sufficiently long value), the statistical model may nonetheless be trained using recorded EMG signals, though the learning process for the model may take longer than if a suitable prediction threshold for the motor task or series of motor tasks was set.

Next, process 300 proceeds to act 308, where the data obtained at acts 302 and 304 is combined to create training data used for training a statistical model at act 310. The obtained data may be combined in any suitable way. In some embodiments, each of the EMG signals obtained at act 302 may be associated with an action corresponding to the result of the motor task being performed by the user when the EMG signals were recorded. For example, EMG signals obtained at time greater than the prediction timescale threshold in advance of the user performing a motor task may be associated with a "no action" label and EMG signals obtained between a time corresponding to the prediction timescale threshold amount before the onset of the motor task and the onset of the motor task may be labeled with the task that was performed by the user. In this way, the statistical model may be trained to predict the occurrence of an action within the prediction timescale threshold of time into the future.

Act 308 is further illustrated in Table 1, which shows that EMG signals obtained at a time greater than the prediction timescale threshold in advance of a user pressing the button "A" are labeled with the name of the action (i.e., "A"), whereas EMG signals obtained earlier than the predication timescale threshold are labeled with the label "no action." In this example, the prediction timescale threshold is at a time between when the EMG signals $x_3$ and $x_4$ were recorded.

TABLE 1

| No Action | No Action | No Action | A | A | A | A |
|---|---|---|---|---|---|---|
| $x_1$ | $x_2$ | $x_3$ | $x_4$ | $x_5$ | $x_6$ | $x_7$ |

Training data consisting of EMG signals $x_1 \ldots x_7$ recorded by EMG sensors worn by a user after the user is instructed to push the button "A" and before the user pushed this button. The EMG signals are associated with corresponding actions including "A" and "no-action."

As a non-limiting example, the EMG signals obtained at act 302 for a particular user may comprise a sequence of vectors $\{x_k | 1 \leq k \leq K\}$ generated using measurements obtained at time points $t_1, t_2, \ldots, t_K$, where the ith component of vector $x_j$ is a value measured by the ith EMG sensor at time $t_j$ and/or derived from the value measured by the ith EMG sensor at time $t_j$. Let M denote the prediction timescale threshold. If the user performed the task (e.g., pressed the button "A" that the user was instructed to press) at time T, then any vector $x_k$ obtained at a time $t_k$ that occurs within M of T (i.e., $|T-t_k| \leq M$) may be associated with the result of the task (e.g., with information indicating that the user pressed the button "A"). On the other hand, any vector $x_k$ obtained at a time $t_k$ that does not occur within M of T (i.e., $|T-t_k| > M$) may be associated with the "no action" result (e.g., the user did not press the button "A" within the prediction timescale threshold).

Next, process 300 proceeds to act 310, where a statistical model for predicting the onset of a motor task is trained using the training data generated at act 308.

The statistical model being trained may take as input a sequence of data sets each of which comprises an n-dimensional vector of EMG sensor data. The statistical model may provide output that indicates, for each of one or more motor tasks that may be performed by a user, the likelihood or probability that the onset of a motor task will occur within a threshold amount of time in the future. For example, the statistical model may take as input a sequence of vectors $\{x_k | 1 \leq k \leq K\}$ generated using measurements obtained at time points $t_1, t_2, \ldots, t_K$, where the ith component of vector $x_j$ is a value measured by the ith EMG sensor at time $t_j$ and/or derived from the value measured by the ith EMG sensor at time $t_j$. Based on such input, the statistical model may provide output indicating, for each action in a set of actions (which set may include a member corresponding to not taking any action), a probability that the onset of the action will occur within a threshold amount of time in the future, which threshold may be the threshold selected at act 306. As one non-limiting example, the statistical model may be trained to anticipate which one of multiple keys on a keypad the user will press within the threshold amount of time in the future. In this example, the statistical model may output, for each key on the keypad, a value indicating the probability that the user will press that key within the threshold amount of time in the future. Additionally, the statistical model may provide output indicating the probability that the user will not press any key within the threshold amount of time in the future.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some of the embodiments in which the statistical model is a neural network, the neural network may include a softmax layer such that the outputs add up to one and may be interpreted as probabilities. The output of the softmax layer may be a set of values corresponding to a respective set of actions, with each value indicating a probability that the user will perform a respective action in the set of actions within a threshold amount of time in the future. As one non-limiting example, the output of the softmax layer may be a set of three probabilities (e.g., 0.92, 0.05, and 0.03) indicating the respective probabilities that the user will press one of the keys "A", "B", and "C" on a keypad within a threshold amount of time in the future (e.g., within 250 milliseconds in the future and/or any other suitable threshold, examples of which are provided herein).

It should be appreciated that when the statistical model is a neural network, the neural network is not required to produce outputs that add up to one. For example, instead of a softmax layer, the output layer of the neural network may be a sigmoid layer (which has no restriction that the probabilities add up to one). In such embodiments, the neural network may be trained with a sigmoid cross-entropy cost. Such an implementation may be advantageous in the case when multiple different actions may occur within a threshold amount of time and it is not important to distinguish the order in which these actions occur (e.g., a user may press two buttons at the same time with the threshold amount of time). In some embodiments, any other suitable non-probabilistic multi-class classifier may be used, as aspects of the technology described herein are not limited in this respect.

It should be appreciated that aspects of the technology described herein are not limited to using neural networks, as other types of statistical models may be employed in some embodiments. For example, in some embodiments, the statistical model may comprise a hidden Markov model (HMM), a switching HMM with the switching allowing for toggling among different dynamic systems, dynamic Bayesian networks, and/or any other suitable graphical model having a temporal component. Any such statistical model may be trained at act 310 using the EMG data obtained at act 302.

As another example, in some embodiments, the statistical model may be a classifier taking as input, features derived from the EMG data obtained at act 302. In such embodiments, the classifier may be trained at act 310 using features extracted from the EMG data obtained at act 302. The classifier may be a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the EMG data obtained at act 302 in any suitable way. For example, the EMG data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the EMG data may be transformed using a wavelet transform and the resulting wavelet coefficients may be provided as inputs to the classifier.

In some embodiments, at act 310, values for parameters of the statistical model may be estimated from the training data generated at act 308. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

Next, process 300 proceeds to act 312, where an operating threshold is determined for the statistical model generated at act 310. The operating threshold may be used for interpreting the output of the statistical model when predicting whether the onset of a particular action will occur in a threshold amount of time in the future. For example, when the statistical model provides a set of values, each of which indicates the probability that the onset of a respective action will occur within a threshold amount of time (e.g., as set by the prediction timescale threshold), the probabilities may be compared to the operating threshold and a prediction may be made based on the comparison. For example, it may be predicted that the user will perform a particular action within the threshold amount of time when the probability for that particular action exceeds the operating threshold.

As an example, suppose that the output of the statistical model is a set of three probability values (e.g., 0.8, 0.15, and 0.05) indicating the respective probabilities that the user will press one of the keys "A", "B", and "C" on a keypad within a threshold amount of time in the future and that the operating threshold is set at 0.75. Because 0.8 is greater than the operating threshold of 0.75, a prediction may be made that the user will press the key "A" within the threshold amount of time. On the other hand, if the operating threshold was set to be greater than 0.8 (e.g., 0.9), a prediction may be made that the user will not press any of the keys "A," "B," and "C" because the probability values in the output vector of the statistical model are all less than the operating threshold.

In some embodiments, the operating threshold may be determined, at act 312, by characterizing performance of the trained statistical model using at least some of the EMG data obtained at act 302 for different candidate operating thresholds. In some embodiments, at least some of the EMG data obtained at act 302 may be held out and not used to train the statistical model at act 310. The held out data may be used for determining the operating threshold at act 312 of process 300 at least in part by characterizing performance of the trained statistical model for different candidate operating thresholds.

The inventors have appreciated that certain performance characteristics of the statistical model (e.g., false positive rate and the mean anticipation time) may depend on the value of the operating threshold used. The mean anticipation time may indicate how far in advance of when the predicted action is to take place, on average, the statistical model may be able to correctly predict that the user will perform the predicted action. In some embodiments, the held out EMG data may be used to calculate at least one performance characteristic (e.g., false positive rate, false negative rate, true positive rate, true negative rate, positive predictive value, negative predictive value, mean anticipation time, any other performance characteristic that can be derived from these quantities, etc.) for each of the different candidate operating thresholds. An operating threshold may then be selected based on the analysis of the held out data and target performance characteristics. For example, a false positive rate and a mean anticipation time may be obtained, using held out EMG data, for each one of multiple different operating thresholds. Based on a target false positive rate (e.g., 15%) and a target mean anticipation time (e.g., 150 milliseconds), the candidate operating threshold associated with a false positive rate closest to the false positive rate and a mean anticipation time closest to the target mean anticipation time may be selected. In some embodiments, a user may specify (e.g., via a user interface) at least one performance characteristic for a task to be performed and the operating threshold may be determined based on the specified at least one performance characteristic.

It should also be appreciated that, in some embodiments, when the statistical model is trained to predict the onset of any one of multiple different actions, different operating thresholds may be used for different actions. For example, when a statistical model is trained to predict whether a user will press one of two different buttons, different operating thresholds may be used for the different buttons. Using different operating thresholds is especially valuable in applications where there are different (e.g., greater or lesser) benefits for anticipating different actions and different (e.g., greater or lesser) costs for false positives.

Next, process 300 proceeds to act 314, where the trained statistical model and/or the operating threshold are stored (e.g., in datastore 214). The trained statistical model and/or operating threshold may be stored using any suitable format, as aspects of the technology described herein are not limited in this respect. In this way, the statistical model and operating threshold generated during execution of process 300 may be used at a later time, for example, in accordance with the process described with reference to FIG. 4.

It should be appreciated that process 300 is illustrative and that variations of the process are contemplated. For example, although in the illustrated embodiment, the statistical model is trained to predict whether a motor action will occur within a threshold amount of time, in other embodiments, the statistical model may be trained to output a distribution over time, indicating probabilities that the motor action will occur at various time points in the future. Such a distribution may be discrete (e.g., specified via a point mass function) or a continuous distribution (e.g., specified via a probability density function). Such a distribution may be used to determine whether a motor action will occur with a threshold amount of time by summing or integrating the distribution as appropriate (e.g., integrating the distribution to determine the amount of probability mass to the right of the threshold).

As another example, although in the illustrated embodiment, the statistical model is trained to output a probability that an action occurs within a threshold amount of time, in other embodiments, the statistical model may be configured to output any suitable type of output indicating a prediction of whether the action will occur within the threshold amount of time. Such a prediction need not be a probability. For example, such a prediction may be binary (e.g., yes or no) indicating whether the output action will or will not occur within the threshold amount of time. As another example, such a prediction may be numeric, but not a probability in that the prediction may be a value greater than one (e.g., an un-normalized likelihood). In embodiments where the prediction output by the statistical model is not a probability value, the operating threshold may be replaced by another suitable hyper-parameter allowing for controlling the tradeoff between a performance measure and mean anticipation rate or may be omitted altogether.

Figure 4:
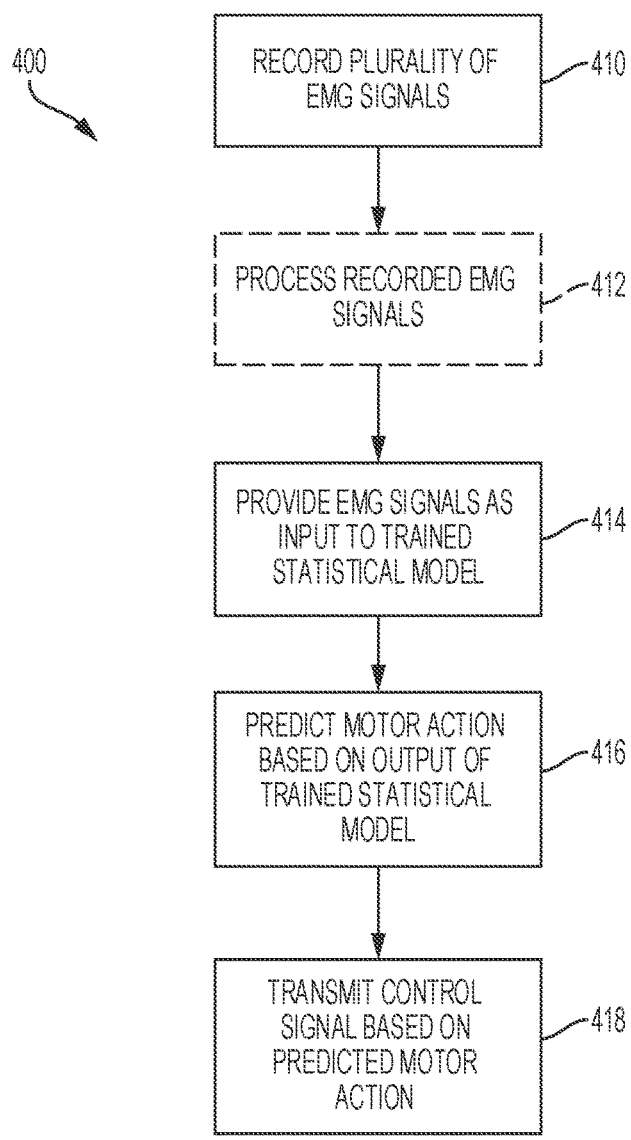
FIG. 4 is a flowchart of an illustrative process for using a trained statistical model to predict the onset of one or more motor tasks using neuromuscular signals, in accordance with some embodiments of the technology described herein.

FIG. 4 illustrates a process 400 for predicting a motor action performed by a user based on recorded EMG signals and a trained statistical model in accordance with some embodiments. Although process 400 is described herein with respect to EMG signals, it should be appreciated that process 400 may be used to predict a motor action performed by a user based on any recorded neuromuscular signals including, but not limited to, EMG signals, MMG signals, SMG signals, or any suitable combination thereof and a trained statistical model trained on such neuromuscular signals.

Process 400 begins in act 410, where EMG signals are recorded from a plurality of EMG sensors arranged on or near the surface of a user's body to record neuromuscular activity as the user performs a motor action. In one example described above, the plurality of EMG sensors are arranged circumferentially (or otherwise oriented) on wearable device configured to be worn on or around a part of the user's body. In some embodiments, the plurality of EMG signals is recorded continuously as a user wears the wearable device including the plurality of EMG sensors. Process 400 then proceeds to act 412, where the raw EMG signals recorded by electrodes in the EMG sensors are optionally processed. For example, the EMG signals may be processed using amplification, filtering, or other types of signal processing (e.g., rectification). In some embodiments, filtering includes temporal filtering implemented using convolution operations and/or equivalent operations in the frequency domain (e.g., after the application of a discrete Fourier transform).

Process 400 then proceeds to act 414, where the EMG signals are provided as input to a statistical model (e.g., a neural network) trained using one or more of the techniques described above in connection with process 300. In some embodiments that continuously record EMG signals, the continuously recorded EMG signals (raw or processed) may be continuously or periodically provided as input to the trained statistical model for prediction of the onset of one or more motor actions performed by the user. As discussed above, in some embodiments, the trained statistical model is a user-independent model trained based on EMG measurements from a plurality of users. In other embodiments, the trained model is a user-dependent model trained on EMG data recorded from the individual user data from which the EMG data is recorded in act 410.

After the trained statistical model receives the EMG data as a set of input parameters, process 400 proceeds to act 416, where the probability of one or more motor actions occurring within a particular time threshold (e.g., the prediction timescale threshold discussed above) is output from the trained statistical model. Also, as discussed above, in some embodiments, the output of the trained statistical model may be a set of probability values (e.g., 0.8, 0.15, and 0.05) indicating the respective probabilities that the user will perform a respective action within a threshold amount of time in the future. The prediction of whether and/or what motor action the user will perform within the threshold amount of time may be determined by comparing the output set of probability values with an operating threshold set for a particular task or application. Non-limiting examples of setting an operating threshold for predicting one or more motor actions are discussed above. In embodiments, where the output of the statistical model is a non-probabilistic prediction, another suitable hyper-parameter may be used instead of the operating threshold to optimize across tradeoffs in performance characteristics, as discussed above.

After a motor action is predicted in act 416, process 400 proceeds to act 418, where a control signal is transmitted to a device based, at least in part, on the predicted motor action. Preferably the control signal is transmitted to the device as soon as possible following the prediction in act 416 to increase the amount of time between when the control signal based on the prediction is sent to the device and the time when the control signal would have been sent had the control signal been sent in response to completion of the motor action.

As discussed briefly above, in some embodiments at least some of the continuously recorded EMG data may be used to retrain the statistical model (or train the statistical model de novo) to enable the model to learn the statistical relationships between neuromuscular activity recorded by the EMG sensors and motor actions performed by a particular user. Continuous training of the statistical model may result in improved performance of the model in predicting actions that are performed by the user in a consistent manner.

Although process 400 is described herein as being performed after process 300 has completed and a statistical model has been trained, in some embodiments, process 300 and 400 may be performed together. For example, the statistical model may be trained in real-time, as a user is interacting with a control interface of a device and the trained statistical model may be used as soon as the model has been trained sufficiently to provide reliable predictions.

In the examples discussed above, aspects of the technology are described in the context of predicting the onset of single motor task (e.g., the probability of whether the user will press a button or not) or predicting the onset of a motor task from among a plurality of motor tasks (e.g., the probability of whether the user will press a particular button from among three buttons). In other embodiments, a statistical model trained in accordance with one or more of the techniques described herein may be used to predict the probability that the user will perform a sequence of motor actions. For example, rather than only predicting whether a user pressed button "A," "B," or "C," some embodiments are directed to predicting whether the user pressed the sequence of buttons "ABC," "ABA" or "CAB." Although the process of selecting data to train the statistical model may differ from the examples described above, the process of training the model, selecting a prediction timescale threshold and an operating threshold proceed similarly in embodiment in which a sequence of motor actions is predicted.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed.

Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A control system, comprising:
a plurality of sensors configured to continuously record a plurality of neuromuscular signals from a user; and
at least one computer processor programmed to:
provide as input to a trained statistical model, the plurality of neuromuscular signals and/or information based on the plurality of neuromuscular signals, wherein the trained statistical model was trained based, at least in part, on neuromuscular data recorded during at least one previous performance of a motor action by one or more users and result data indicating an outcome of the motor action performed by the one or more users, wherein the trained statistical model is configured to predict the onset of the motor action prior to completion of the motor action;
predict, based on an output of the trained statistical model, whether an onset of the motor action will occur within a threshold amount of time; and
send a control signal to at least one device based, at least in part, on the prediction, wherein the control signal is sent to the at least one device prior to completion of the motor action by the user to control an operation of the at least one device.

2. The control system of claim 1, wherein the output of the trained statistical model comprises a probability that the onset of the motor action will occur within the threshold amount of time, and
wherein predicting that an onset of the motor action will occur within a threshold amount of time comprises determining whether the probability is greater than an operating threshold.

3. The control system of claim 2, wherein the at least one computer processor is further programmed to determine the operating threshold based, at least in part, on an analysis of data obtained from neuromuscular signals recorded by at least some of the plurality of sensors.

4. The control system of claim 3, wherein determining the operating threshold comprises:
determining a mean anticipation time based on the data; and
determining the operating threshold based, at least in part, on the mean anticipation time.

5. The control system of claim 2, wherein the at least one computer processor is further programmed to receive at least one performance characteristic for a task to be performed, and wherein the operating threshold is determined based, at least in part, on the received at least one performance characteristic.

6. The control system of claim 5, wherein the at least one performance characteristic includes a performance characteristic selected from the group consisting of a false positive rate, a false negative rate, a true positive rate, a true negative rate, a positive predictive value, a negative predictive value, and a mean anticipation time.

7. The control system of claim 1, wherein the output of the trained statistical model comprises a set of probabilities, each probability in the set indicating a probability that the onset of a respective motor action of a plurality of motor actions will occur within the threshold amount of time, and
wherein predicting that an onset of the motor action will occur within a threshold amount of time comprises determining whether any of the probabilities in the set of probabilities is greater than an operating threshold stored by the system.

8. The control system of claim 1, wherein the output of the trained statistical model comprises a probability that the onset of a sequence of motor actions will occur within the threshold amount of time, and wherein predicting that an onset of the motor action will occur within a threshold amount of time comprises determining whether the probability is greater than an operating threshold.

9. The control system of claim 1, wherein the at least one computer processor is further programmed to retrain the trained statistical model based, at least in part, on at least some of the plurality of neuromuscular signals.

10. The control system of claim 1, wherein the trained statistical model comprises a recurrent neural network.

11. The control system of claim 1, wherein the at least one computer processor is further programmed to:
determine a set of features based on the plurality of neuromuscular signals; and
provide as input to a trained statistical model, the set of features as information based on the plurality of neuromuscular signals,
wherein predicting, based on an output of the trained statistical model, that an onset of the motor action will occur within a threshold amount of time comprises classifying the set of features using the trained statistical model.

12. The control system of claim 1, wherein the plurality of sensors are arranged on a wearable device configured to be worn on or around a body part of the user.

13. The control system of claim 12, wherein the wearable device comprises a flexible or elastic band configured to be worn around the body part of the user.

14. The control system of claim 13, wherein the wearable device comprises an armband configured to be worn around an arm of the user.

15. The control system of claim 1, further comprising hardware circuitry and/or software configured to process the neuromuscular signals prior to being provided as input to the trained statistical model, wherein processing the neuromuscular signals comprises processing selected from the group consisting of amplification, filtering, and rectification.

16. The control system of claim 1, wherein sending the control signal to the at least one device prior to completion of the motor action by the user comprises sending the control signal at least 25 ms prior to the completion of the motor action by the user.

17. The control system of claim 1, wherein the at least one device comprises at least one device selected from the group consisting of a video game system, a consumer electronics device, a manned vehicle, an unmanned vehicle, a robot, and a weapon.

18. The control system of claim 1, wherein the plurality of sensors comprises sensors selected from the group consisting of electromyography (EMG) sensors, mechanomyography (MMG) sensors, and sonomyography (SMG) sensors.

19. A method of predicting an onset of a motor action, the method comprising
providing, as input to a trained statistical model, a plurality of neuromuscular signals recorded from a plurality of sensors arranged on or around a part of a user's body, wherein the trained statistical model was trained based, at least in part, on neuromuscular data recorded during at least one previous performance of a motor action by one or more users and result data indicating an outcome of the motor action performed by the one or more users, wherein the trained statistical model is configured to predict the onset of the motor action prior to completion of the motor action;
predicting, using at least one computer processor, whether an onset of the motor action will occur within a threshold amount of time; and
sending a control signal to at least one device based, at least in part, on the prediction, wherein the control signal is sent to the at least one device prior to completion of the motor action by the user to control an operation of the at least one device.

20. A computer system for training a statistical model to predict an onset of a motor action based, at least in part, on neuromuscular signal data, the computer system comprising:
an input interface configured to:
receive the neuromuscular signal data recorded during performance of a motor action performed by one or more users;
receive result data indicating an outcome of the motor action performed by the one or more users; and
at least one storage device configured to store a plurality of instructions that, when executed by at least one computer processor perform a method of:
generating training data based, at least on part, on the received neuromuscular signal data and the received result data;
training the statistical model using at least some of the generated training data to output a trained statistical model;
determining an operating threshold used to interpret output of the trained statistical model; and
storing, by the at least one storage device, the trained statistical model and the operating threshold, wherein the trained statistical model is configured to predict the onset of the motor action prior to completion of the motor action by a user.

* * * * *